(12) United States Patent
Alzaidi

(10) Patent No.: US 9,020,099 B1
(45) Date of Patent: Apr. 28, 2015

(54) MINIATURIZED PIPE INSPECTION SYSTEM FOR MEASURING CORROSION AND SCALE IN SMALL PIPES

(71) Applicant: King Abdulaziz University, Jeddah (SA)

(72) Inventor: Samir Abdul-Majid Alzaidi, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 14/559,873

(22) Filed: Dec. 3, 2014

(51) Int. Cl.
 G01N 23/203 (2006.01)
 G01T 1/36 (2006.01)
 H01J 40/16 (2006.01)
(52) U.S. Cl.
 CPC ............. *G01N 23/203* (2013.01); *G01T 1/362* (2013.01); *H01J 40/16* (2013.01)
(58) Field of Classification Search
 CPC ... G01N 23/203; G01N 23/201; G01N 23/20; G01B 15/02; G01V 5/0025; G01V 5/0016; G01V 5/0066
 USPC ................................................ 378/70, 86–90
 See application file for complete search history.

(56) References Cited

U.S. PATENT DOCUMENTS

| 4,580,053 | A | 4/1986 | Snyder |
| 5,195,117 | A | 3/1993 | Ong |
| 5,970,116 | A | 10/1999 | Dueholm et al. |
| 6,252,930 | B1 | 6/2001 | MacKenzie |
| 6,421,418 | B1 | 7/2002 | Schulte |
| 6,895,074 | B2 | 5/2005 | Benedetti |
| 8,792,611 | B2 * | 7/2014 | Cahill ............................ 378/54 |

FOREIGN PATENT DOCUMENTS

| WO | WO 9322661 A1 | 11/1993 |
| WO | WO 9733141 A1 | 9/1997 |
| WO | WO 9914581 A1 | 3/1999 |

OTHER PUBLICATIONS

Samir Abdul-Majid and Waleed AbulFaraj, "Asphalt and Paraffin Scale Deposit Measurement by Neutron Back Diffusion Using 252Cf and 241Am-Be Sources", 3rd MENDT—Middle East Nondestructive Testing Conference & Exhibition—Nov. 27-30, 2005 Bahrain, Manama.

Samir Abdul-Majid, "Simultaneous Determination of Iron Pipe Wall and Scale Thicknesses by Prompt Gamma Emission Method", 3rd MENDT—Middle East Nondestructive Testing Conference & Exhibition—Nov. 27-30, 2005 Bahrain, Manama.

Samir Abdul-Majid and Waleed H. Abulfaraj, Gamma Ray Interaction and "Neutron Capture Gamma Ray Technique for the Analysis of Cu—Ni Alloys", 3rd MENDT—Middle East Nondestructive Testing Conference & Exhibition Nov. 27-30, 2005 Bahrain, Manama.

* cited by examiner

*Primary Examiner* — Jurie Yun
(74) *Attorney, Agent, or Firm* — Richard C. Litman

(57) ABSTRACT

The miniaturized pipe inspection system for measuring corrosion and scale in small pipes utilizes scattered radiation, which is measured by high efficiency solid scintillation gamma detector/spectrometer inserted inside the tube and separated from its bulky photomultiplier tube (PMT) and associated electronics by light pipe or fiber optic cable whose diameter can be very small. The light signal produced in the scintillation material is transmitted through the light pipe to outside the pipe to be inspected, where a PMT and electronic components including gamma ray energy analyzers are located. Gamma spectroscopy combined with gamma counting allows for multiple gamma ray primary and multiple backscattered radiation, thereby yielding high accuracy and high reliability of obtained corrosion, erosion and deposits data.

15 Claims, 9 Drawing Sheets

MINIATURIZED PIPE INSPECTION SYSTEM FOR MEASURING CORROSION AND SCALE IN SMALL PIPES

BACKGROUND OF THE INVENTION

1. Field of the Invention

The present invention relates to a system for conducting in situ and non-destructive measuring of the thickness of coatings, and more particularly to a miniaturized pipe inspection system for measuring corrosion and scale in small pipes that uses backscattering of gamma rays to inspect corrosion and scale substrates disposed inside small pipes, which may be twisted, bent, or have irregular cross-sections.

2. Description of the Related Art

To detect corrosion in small pipes, such as heat exchanger pipes, radiographic techniques are sometimes used in which one radioactive source is inserted inside one tube and radiographic film is inserted inside an adjacent or nearby tube. This technique is time-consuming and does not provide adequate information, and has a limitation on the size of radiographic films that can be used. Moreover, a high radioactivity source, on the order of many Curies, is usually used, which is associated with radiation hazard in the inspection process.

Gamma ray attenuation is also used in which a radioactive source is inserted in one pipe and a radiation detector is put into an adjacent or nearby tube and attenuation in the tube wall is measured. The detector used in these cases is usually a Geiger-Muller counter. Besides being time-consuming, this technique cannot predict which pipe has the defect, the one in which the source is inserted or the one in which the detector is inserted. And because Geiger counters are gas-filled detectors, it usually has very low efficiency, typically several orders of magnitude compared to solid scintillation detectors. Moreover, Geiger detectors are counters only, providing no information on the spectrum of attenuated rays, and indiscriminately responding to both direct and scattered radiation. This tends to produce errors in the registered counts. Radiation detectors/spectrometers, such as scintillation detectors, are more useful, but cannot be inserted inside small diameter tubes because the photo-multiplier tube (PMT) and associated electronics are often much larger in size than the tube diameter. Solid state detectors are very expensive, and their associated electronic components are large, expensive, and not useful for field work. Other techniques are used, in which a neutron source is inserted inside the pipe to activate the pipe wall or surrounding materials, and then measuring the induced radioactivity in walls by gamma detector. Again, this technique can be used in large sewage buried pipes, but cannot be used in pipes of heat exchangers. Copper, nickel or iron, the material of the tubes, cannot be activated easily by a small neutron source because of their very small neutron absorption cross section. Moreover, gamma rays need to be measured by high efficiency detectors that cannot be inserted inside heat exchangers.

Eddy current and ultrasound techniques can be used, but the inside of the pipe needs to be well prepared and clean, which makes the inspection process more difficult and time-consuming.

It should be clearly mentioned here that none of the existing techniques work for twisted pipes in heat exchangers. Also, it is very difficult to use existing techniques for inspecting pipes whose cross section is not circular, or for inspecting bent pipes.

Thus, a miniaturized pipe inspection system for measuring corrosion and scale in small pipes solving the aforementioned problems is desired.

SUMMARY OF THE INVENTION

The miniaturized pipe inspection system for measuring corrosion and scale in small pipes provides a system for inspecting twisted pipes, pipes whose cross sections are not circular, circular pipes, prepared or unprepared pipes, straight pipes, and bended pipes from the inside, for instance, heat exchangers or similar pipes. These pipes usually have small diameters of about one centimeter, and for inspection from inside, only small-size equipment can be used. It includes introducing one or more radioactive source of gamma rays that give one or more than one primary radiation and a scintillation detector into the pipe.

A light pipe is connected to the scintillation detector to transfer a light signal to a PMT (photomultiplier tube), gamma spectrometry devices, and nuclear electronics put outside the pipe for analyzing the back-scattered gamma rays. Because high detection sensitivity is used, only very small radioactivity on the order of micro-curies is used. Gamma rays interact with the pipe wall, and scattered radiation is measured by the scintillation detector. The amount of back-scattered radiation is proportional to the pipe wall thickness and/or density. Each primary radiation produces its own scattered peak that can be separated from other scattered peaks or primary peaks by the gamma analysis system. Each backscatter peak counts, as well as total backscatter peak counts, provides information on corrosion, erosion, or deposits in the pipes. This provides higher accuracy and reliability and diversity of application of the system for pipes of different thicknesses and material.

A spring is provided for biasing the radioactive source(s) and the scintillation detector towards a wall of the pipe or tube in order to provide information from the pipe region near the radioactive source(s) and detector. The inspection system can be put in rotational and translational movements for full scanning or imaging of the pipe.

A shield may or may not be put between the radioactive source of gamma rays and the scintillation detector. The system has high sensitivity for wider range of pipe wall thicknesses and materials and does not need surface preparation.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1A:
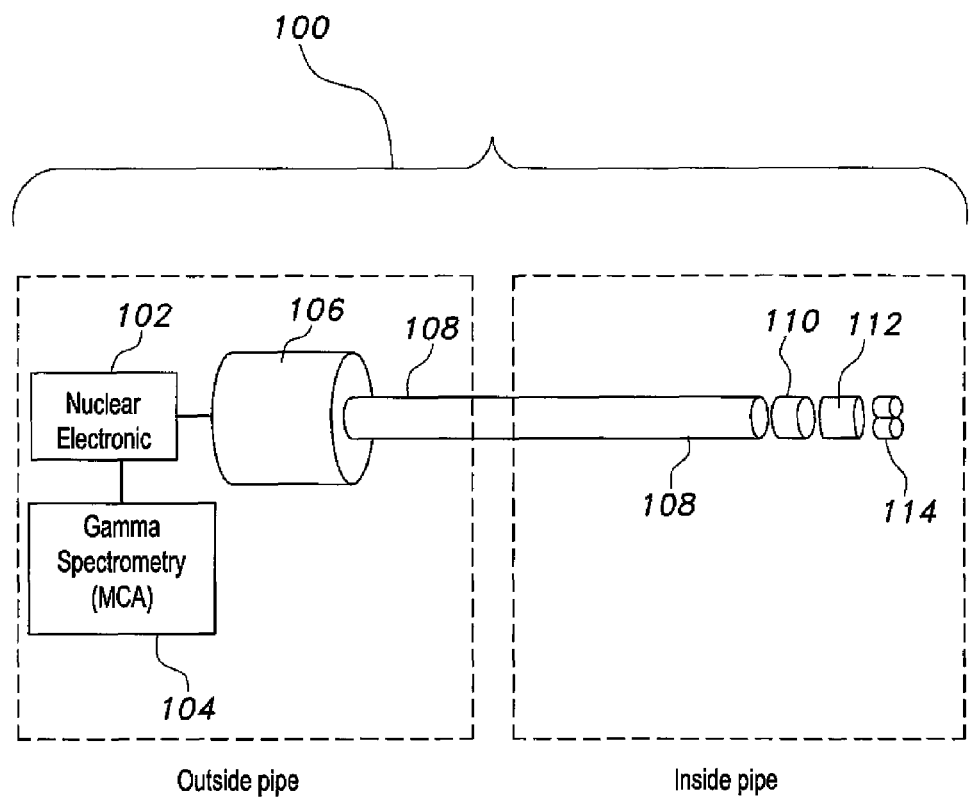
FIG. 1A is a block diagram of the miniaturized pipe inspection system for measuring corrosion and scale in small pipes according to the present invention.
Figure 1B:
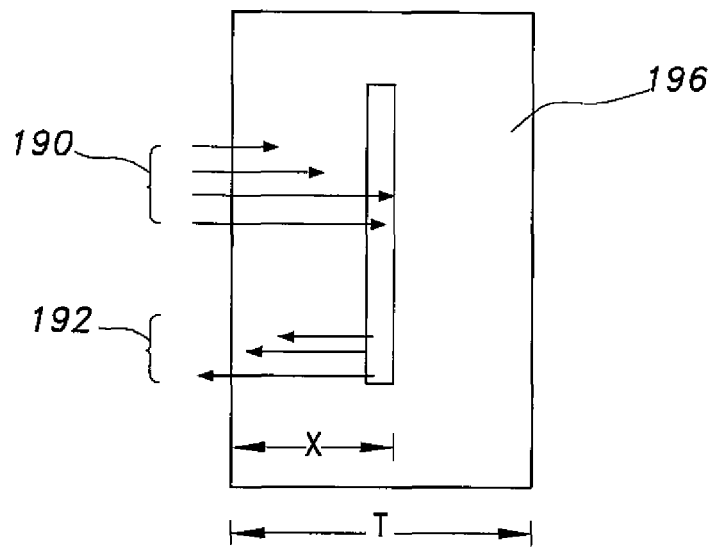
FIG. 1B is a schematic diagram showing the relationship between incident and scattered gamma rays according to the present invention.
Figure 2:
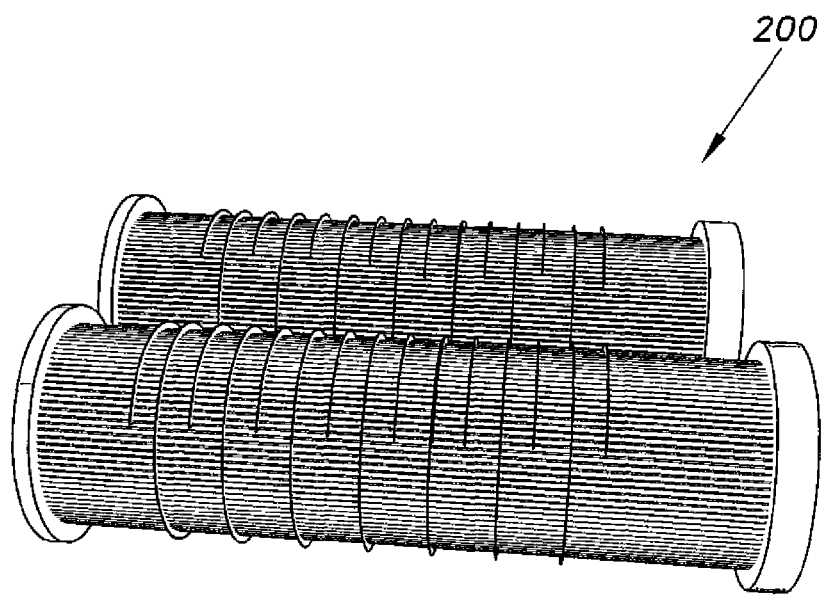
FIG. 2 is a perspective view showing a heat exchanger that can be inspected using the miniaturized pipe inspection system for measuring corrosion and scale in small pipes according to the present invention.

The miniaturized pipe inspection system 100 (shown in FIG. 1A) provides a system for inspecting twisted pipes, pipes whose cross sections are not circular, circular pipes, prepared or unprepared pipes, straight pipes, and bended pipes from the inside the pipe for heat exchangers, such as the heat exchanger tube bundle 200 shown in FIG. 2, or similar pipes. Referring to FIG. 1B, when gamma rays 190 are caused to be incident on a pipe wall 196, attenuation takes place in incident rays as well as the reflected gamma rays 192. The magnitude of attenuation depends on the energy of the gamma rays and the atomic number and density of the material. The attenuation to distance X of incident gamma rays 190 within the wall for a parallel beam is proportional to:

$$\text{Exp}(-\mu X), \tag{1}$$

where $\mu$ is the linear attenuation coefficient of the incident ray. A portion of the intensity is scattered due to Compton interaction. Characteristic x-rays, as well as annihilation radiation of 0.511 MeV, are also emitted. The annihilation radiation is emitted only if the incident primary energy is greater than 1.022 MeV. Scattering takes place from all inside layers of the wall and undergoes higher attenuation in its path back because its energy is lower than that of the primary incident radiation. Radiation, therefore, undergoes double attenuation. Taking the special case of a parallel component of back-scattered radiation, the back-scattered gamma rays from a distance x undergo attenuation proportional to:

$$\text{Exp}(-\mu' X), \tag{2}$$

where $\mu'$ is the linear attenuation coefficient of the back-scattered rays. The total attenuation of incident as well as back-scattered radiation at a specific distance x will be proportional to:

$$\text{Exp}[(-\mu'+\mu)\cdot X]. \tag{3}$$

The intensity of backscattered gamma rays of specific energy due to interaction with material of thickness T will be proportional to:

$$\{1-\text{Exp}[(-\mu'+\mu)T]\}, \tag{4}$$

or to:

$$\{1-\text{Exp}[-(\mu_m'+\mu_m)T\rho]\}, \tag{5}$$

where $\mu_m'$ and $\mu_m$ are the mass attenuation coefficients of scattered and incident beams, and $\rho$ is the material density. Back-scattered radiation increases with thickness sharply at a small thickness T, then reaches saturation at high thicknesses. Saturation depends on the gamma ray energy and the atomic number and density of the wall materials. With lower incident energy and/or higher atomic number of wall materials, saturation will be reached at smaller thicknesses. This will be useful for thinner or low atomic number pipe inspections. With higher incident energy, saturation can be reached at higher wall thickness and/or low atomic number pipe materials. This is useful for application at higher thickness and higher atomic number pipes. The present system 100 uses these phenomena to measure changes of pipe wall thickness due to corrosion. Moreover, the existence of deposits on the wall will change the intensity of scattered rays, and therefore can be detected.

Referring to FIGS. 1A, 4, 5, 6, 7, 8, 9, and 14, the system 100 provides inspection using the scattered gamma rays inside the tube 5. The inspection system 100 includes at least one radioactive source 114, and may include a gamma shield 112 disposed between the radioactive source 114 and a scintillation detector 110. A light pipe or a fiber optic cable 108 is configured to pick up signals from the scintillation detector 110. A spring system 404 is disposed in the pipe in a manner that pushes the radioactive source 114, detector 110 and shield 112 (if a shield is used) combination 414 towards the pipe wall. A photo-multiplier tube (PMT) 106 or similar device amplifies the detected scintillation signal. Nuclear electronics 102 and a gamma ray multi-channel analyzer 104 perform statistics and analysis on the amplified signal output from the photo-multiplier tube (PMT) 106. Only the light pipe 108, scintillation detector 110, shield 112, and radiation source 114 are disposed inside the pipe 5 (tube to be measured). It may also be possible to insert the PMT 106 if it is small enough. The light pipe 108 can have a very small diameter, down to a fraction of a millimeter, and can be inserted inside the tube together with the radioactive source 114, detector 110 and shield 112 (as shown in FIG. 1A) to transfer the light signal outside the pipe or tube. The nuclear electronics and energy analysis systems associated with the scintillation detection are bulky and much larger than the tube diameter, and cannot be inserted inside the tube or pipe.

Figure 3:
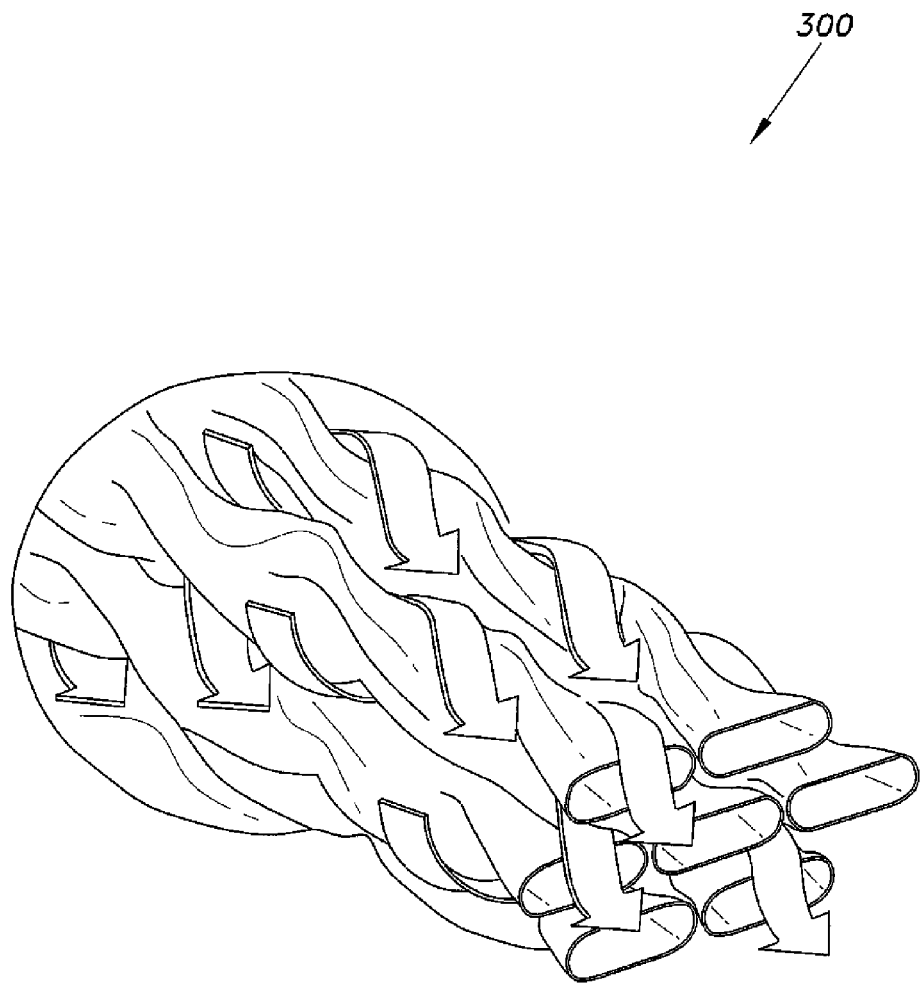
FIG. 3 is a perspective view of twisted tubes, broken off to show the cross-sectional shape and showing sensor locations of the heat exchanger that can be inspected using the miniaturized pipe inspection system for measuring corrosion and scale in small pipes according to the present invention.
Figure 6:
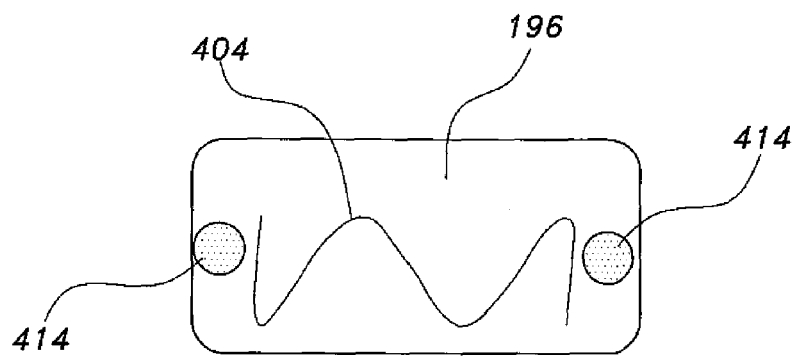
FIG. 6 is a diagrammatic cross section of a rectangular heat exchanger, showing sensor placement for a miniaturized pipe inspection system for measuring corrosion and scale in small pipes according to the present invention.

The photo-multiplier tube 106, nuclear electronics and energy analysis systems associated with the scintillation detection are disposed outside the pipe, while the source(s) 114, scintillation detector 110 and light pipe 108 are disposed inside the tube to be measured, as shown in FIG. 1A. As shown in FIG. 6, the biasing spring 404 is used to keep the detection system 414 in contact with the wall 196 of the tube undergoing measurement. The system 100 will yield information mainly from the wall region adjacent to the detector and source combination 414. This is useful, particularly when pipes are not circular, such as the oval cross-section pipe 500 shown in FIG. 5, substantially rectangular cross-section pipe 600 shown in FIG. 6, and twisted pipe heat exchanger 300, shown in FIG. 3.

Figure 4:
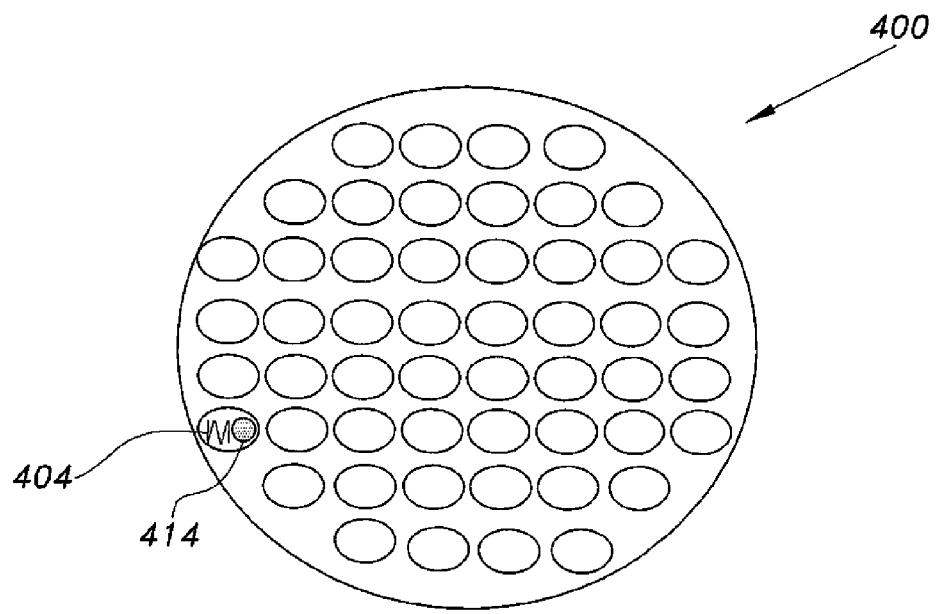
FIG. 4 is a diagrammatic cross section of a heat exchanger with circular tubes, showing sensor placement for a miniaturized pipe inspection system for measuring corrosion and scale in small pipes according to the present invention.
Figure 5:
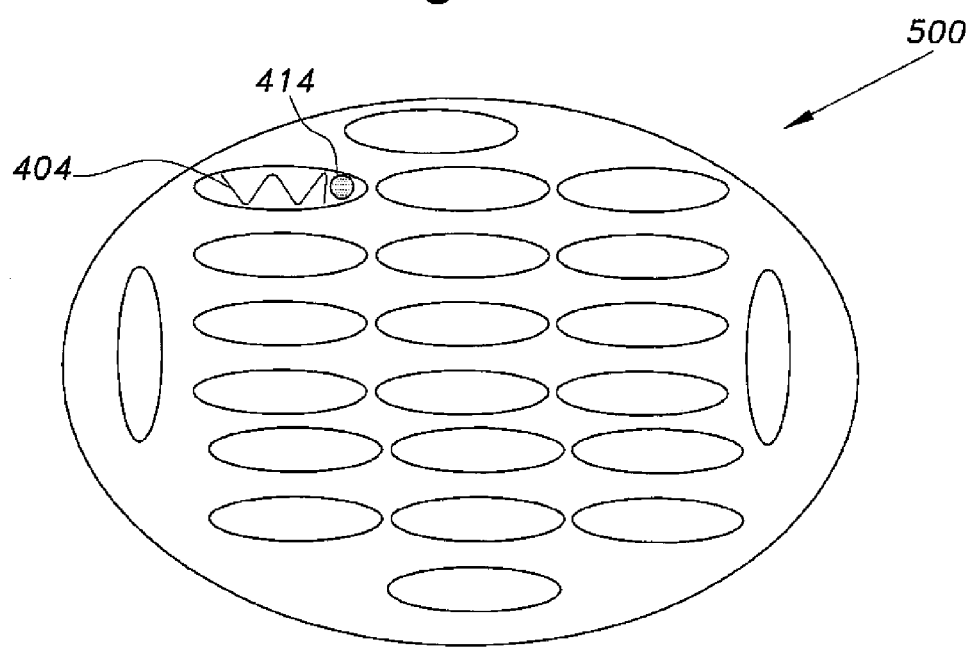
FIG. 5 is a diagrammatic cross section of a heat exchanger with oval tubes, showing sensor placement for a miniaturized pipe inspection system for measuring corrosion and scale in small pipes according to the present invention.

The biasing spring 404 and detector/source combination 414 is also effective for wall contact in the circular tube heat exchanger 400, shown in FIG. 4. The scintillation detector 110, the light pipe 108, and the PMT 106 are light-tight. The shield 112 prevents primary gamma rays emitted from the radioactive source(s) 114 from directly reaching the scintillation detector 110. Nevertheless, the system 100 maintains operable functionality, even when the shield 112 is not present.

Figure 7:
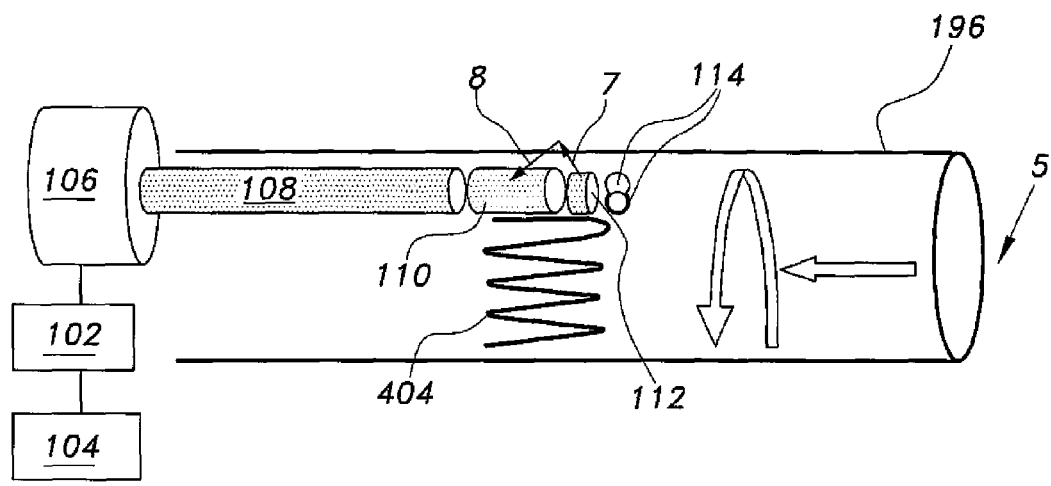
FIG. 7 is a diagrammatic perspective view showing component placement of the miniaturized pipe inspection system for measuring corrosion and scale in small pipes according to the present invention with respect to the pipe to be inspected.
Figure 8:
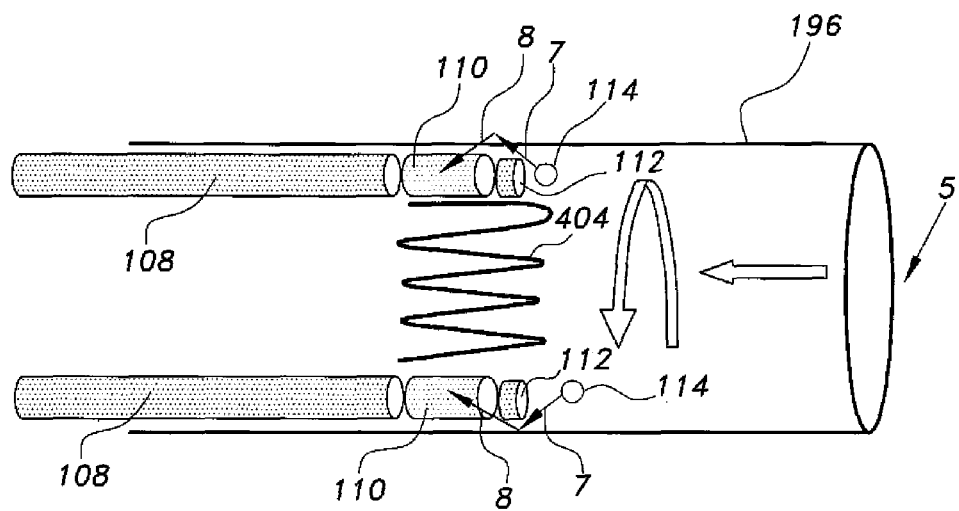
FIG. 8 is a diagrammatic perspective view showing dual light pipes component placement of the miniaturized pipe inspection system for measuring corrosion and scale in small pipes according to the present invention with respect to the pipe to be inspected.

Gamma rays interact with the pipe wall material next to the detector in such a way that some will scatter back to the scintillation detector 110. The amount of scattered rays is proportional to the wall thickness of the pipe 5. Less scattered radiation means less thickness. If corrosion or erosion exists in a region of the pipe, the amount of scattered radiation from that region is less compared to that from a non-corroded region. The emitted radiation 7 and scattered radiations 8 are shown in FIGS. 7 and 8. One or more systems for pipe wall inspection can be utilized. In FIG. 8, the spring 404 biases a dual light-pipe 108 detector 112 and source 114 configuration inside the pipe 5. If there are deposits, the amount of scattered radiation will be different because the density and atomic number of the deposits are different.

Figure 10:
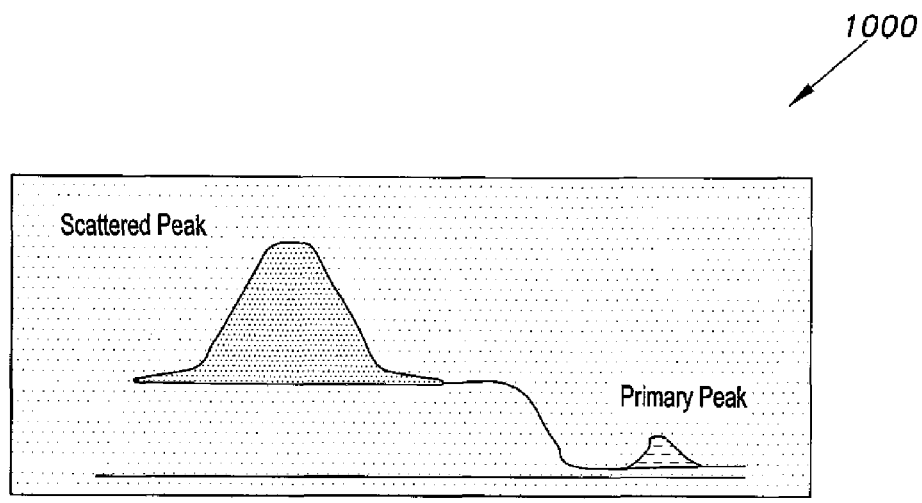
FIG. 10 is a plot showing a scattered peak and primary peak of the measurements obtained using the miniaturized pipe inspection system for measuring corrosion and scale in small pipes according to the present invention when a shield is positioned between the source and detector.

Referring again to FIG. 1A, scattered gamma rays produce light in the scintillation detector 110 that is transmitted through the light pipe or fiber optic cable 108 to the PMT 106. The PMT 106 transmits an electronic signal to the nuclear electronics 102, and the signals from the nuclear electronics 102 are fed into a multi-channel analyzer 104. The output from the multichannel analyzer 104 due to Compton interaction, if shield 112 exists between the detector 110 and the radioactive source 114, will be as shown in plot 1000 of FIG. 10 if a single primary energy source is used. The primary peak will not appear, or will appear very small in this case.

Figure 11:
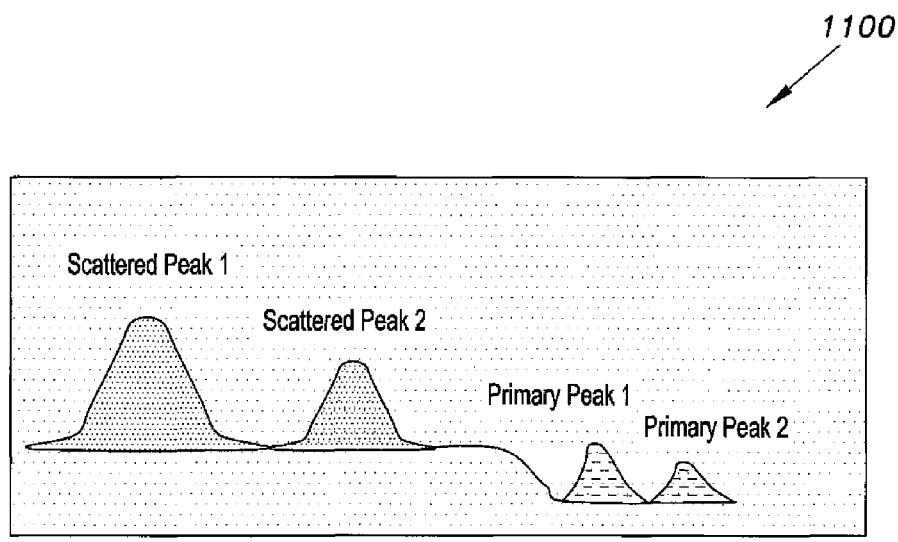
FIG. 11 is a plot showing two scattered peaks and two primary peaks of the measurements obtained using the miniaturized pipe inspection system for measuring corrosion and scale in small pipes according to the present invention when a shield is positioned between the source and detector.

The total counts under the scattered peak (the area under the peak) are proportional to the wall thickness of the region close to the detector. If two primary energy sources (or if a single source that emits two primary energies) are used, the spectrum will be as shown in plot 1100 of FIG. 11. The area under each scattered peak and the total area under all scattered peaks are proportional to the wall thickness. Accordingly, higher precision data can be obtained.

Figure 9:
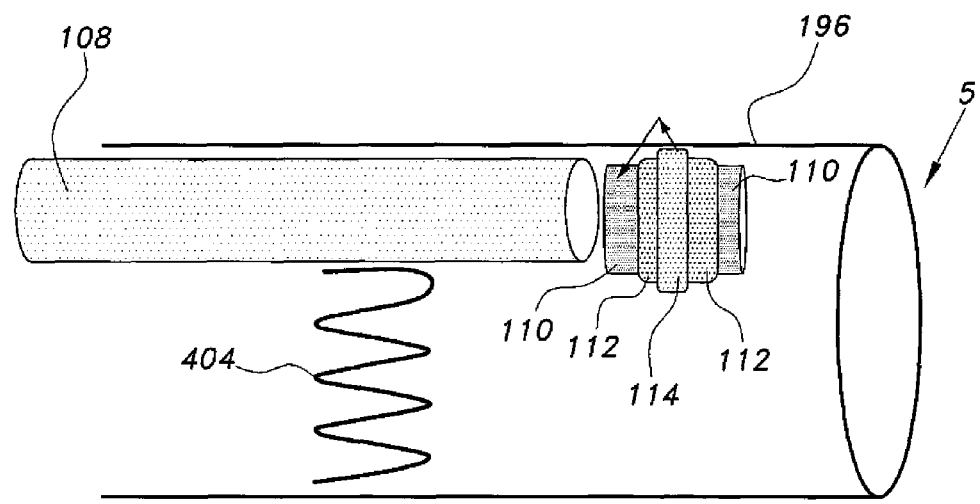
FIG. 9 is a diagrammatic perspective view showing annular configuration of shield, detector and source of the miniaturized pipe inspection system for measuring corrosion and scale in small pipes according to the present invention inside the pipe to be inspected.
Figure 12:
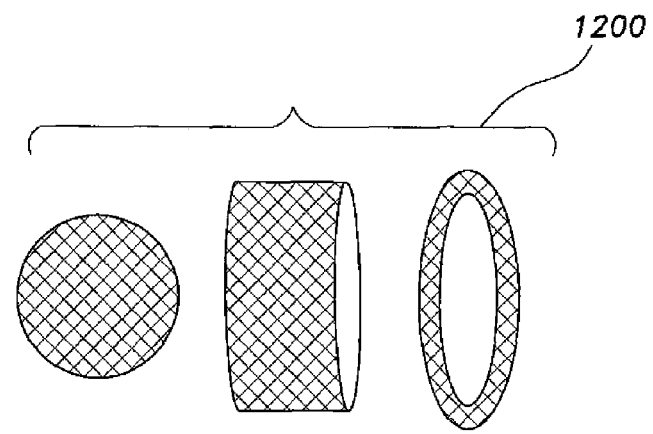
FIG. 12 is a diagrammatic perspective view showing a size and shape comparison of the sources that can be used in a miniaturized pipe inspection system for measuring corrosion and scale in small pipes according to the present invention.

More than one geometry of source 114, shield 112 and detector 110 can be used, such as the exemplary probe configuration shown in FIG. 9, in which the source 114, shield 112 and detector 110 are in concentric relation with each other. The gamma shield 112 forms a collar in contact with and surrounding the scintillation detector 110, while the primary radiation source 114 forms a collar in contact with and surrounding the gamma shield 112. As shown in FIG. 12, alternate source shapes 1200 having a variety of sizes can be used.

Figure 13:
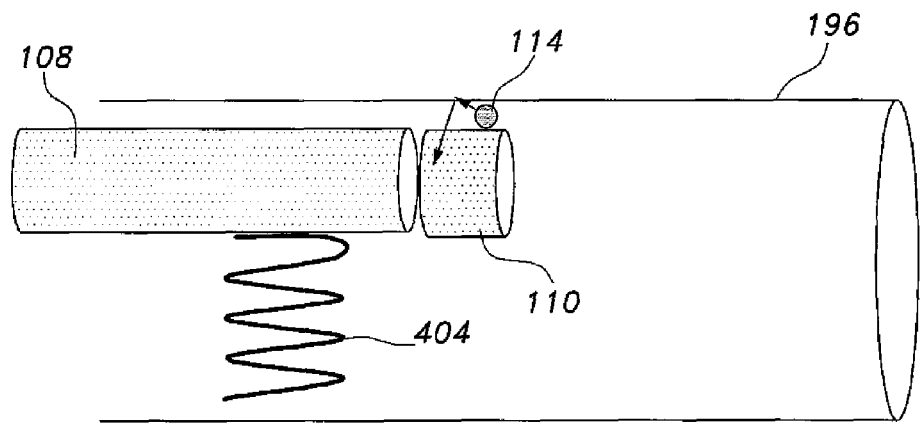
FIG. 13 is a diagrammatic perspective view showing spring, light pipe and source placement inside the pipe in a miniaturized pipe inspection system for measuring corrosion and scale in small pipes according to the present invention.
Figure 14:
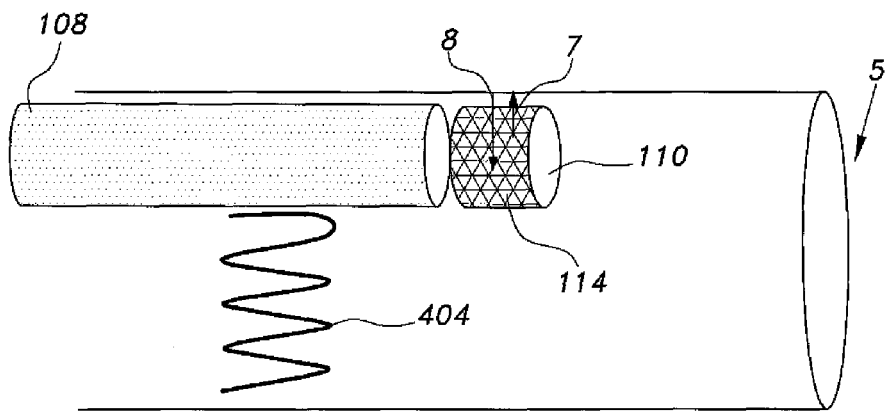
FIG. 14 is a diagrammatic perspective view showing spring, light pipe and an alternative source placement inside the pipe in a miniaturized pipe inspection system for measuring corrosion and scale in small pipes according to the present invention.
Figure 15:
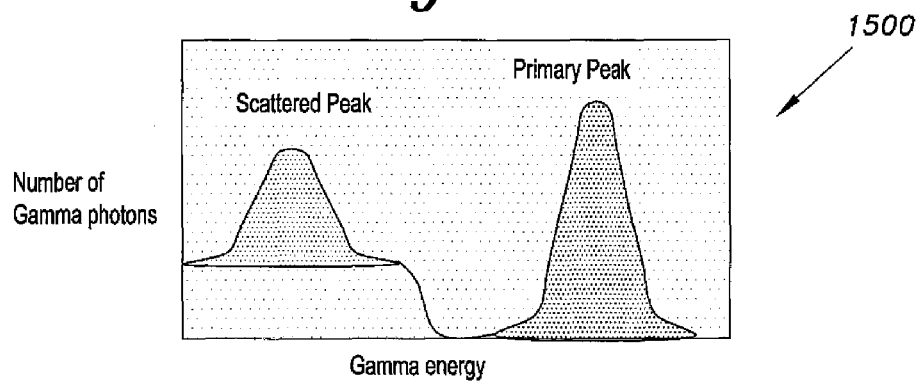
FIG. 15 is a plot showing a spectrum of direct and scattered gamma rays of single primary energy in a miniaturized pipe inspection system for measuring corrosion and scale in small pipes if no shield exists between the source and detector according to the present invention.
Figure 16:
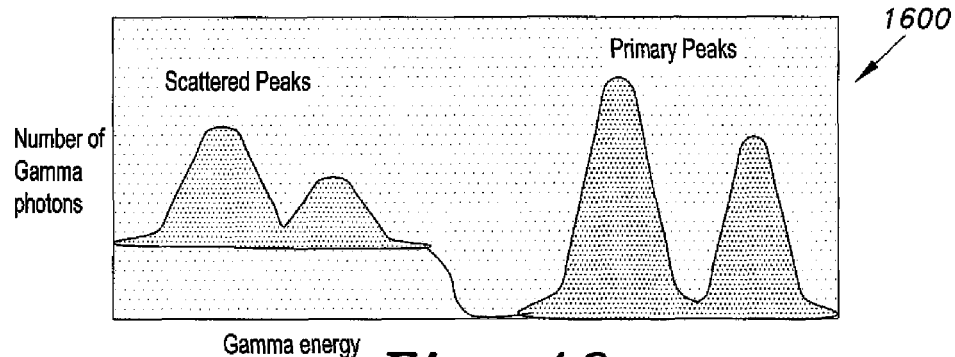
FIG. 16 is a plot showing a spectrum of direct and scattered gamma rays of dual primary energy in a miniaturized pipe inspection system for measuring corrosion and scale in small pipes if no shield exists between the source and detector according to the present invention.

It is possible to use the system without the gamma shield 112, as shown in FIG. 13. The radioactive source 114 is put in direct contact with the scintillation detector 110. Moreover, the detector 110 may be coated with a radioactive source 114, as shown in FIG. 14. The detector will measure both primary and secondary radiation. In this case, the spectrum will be as that shown in plot 1500 of FIG. 15 for a single primary ray, and in plot 1600 of FIG. 16 for two energy primary gamma rays. The total counts under each scattered peak and the sum of total counts under all scattered peaks are proportional to the wall thickness. It is possible to use more than two primary radiation sources if higher accuracy or wider applications are needed.

Scanning can be made inside the pipe or tube 5 by rotation and translation movements of the detection system using a mechanical scanner. Information on the condition of all regions of the pipe or tube 5 can then be found. An image of corrosion from inside can also be made by taking the signals to an image construction system.

As mentioned above, and as can be seen from equations (4) and (5), scattered radiation depends on thickness and density of the pipe wall. It also depends on material atomic and radiation energies, because the parameters $\mu$ and $\mu'$ depend upon these parameters. For low atomic number, small density or small thickness, use of low energy primary radiation is preferred and gives better sensitivities.

If high energy radiation is used, the interaction with wall materials will be small, especially if the material has low atomic number and low density, thereby resulting in low sensitivity. On the other hand, with higher atomic number, higher density or larger thickness higher energy primary radiation should be used. If low energy primary radiation is used, especially with high atomic number and high density, saturation in scattered radiation is reached, causing the radiation not to penetrate the total thickness, and consequently not enough information can be obtained.

With multi-energy primary radiation, there will be multi-scattered radiation. Each primary will have its own scattered radiation that can be separated from other scattered radiation by the gamma spectrometer energy analysis system, such as multichannel analyzer 104.

In this system 100, with more than scattered peaks, there will be a multi-set of data relating to the same wall thickness measurements. By comparison, between the areas under the peak of each scattered radiation, higher accuracy is reached. Also, the system 100 can be used for wider wall types of different atomic number, density and thicknesses, and the inspection system will be more efficient and more accurate. Multi primary gamma rays can be obtained by using a radioactive source that emits multiple primary gamma rays, or by using more than one radioactive source 114.

The system's compact size allows it to be used for heat exchangers or similar pipes that are smaller than one centimeter in diameter. This is possible by use of small diameter scintillation detectors and light pipes with larger size electronic components kept outside the pipe. No existing inspection system based on gamma scattering uses the present system.

With respect to safer micro-curies sources with gamma spectrometry, the system utilizes radioactive source(s) of micro-Curies. It is based on gamma spectrometry and counting and on high-efficiency, solid scintillation detectors. Other radiographic or radiation-based inspection systems utilize radioactive sources of several Curies. The system is, therefore, much safer.

Regarding deposit measurements, a deposit on the pipe wall from inside can be detected, as the interaction, and accordingly, the scattered radiation will differ because of the different density and atomic number of scale compared to pipe wall material. Different signals will be obtained, depending on the nature of the deposit.

In a system for twisted pipes, bent pipes, and tubes that are not circular, use of a biasing spring, if the pipe is a twisted type 300 (FIG. 3) or if its cross-sectional area is not circular (FIGS. 5 & 6), as the case in new heat exchangers, will be essential. The biasing spring 404 pushes the source-detection combination 414 near the wall. This helps in providing information on corrosion or deposits from regions near the detector in the pipes. Other existing systems fail to inspect pipes of this type.

Use of more than one inspection system at the same time (as shown in FIG. 8) is possible for faster counting time and higher accuracy because the inspection device is small. Scanning the whole pipe from inside can provide a complete inside image of the pipe.

It is to be understood that the present invention is not limited to the embodiments described above, but encompasses any and all embodiments within the scope of the following claims.

I claim:

1. A miniaturized pipe inspection system for measuring corrosion and scale in small pipes, comprising:
    a miniaturized detection assembly adapted for insertion inside a pipe for inspection of a wall of the pipe, the detection assembly including:
        at least one primary radiation source of gamma rays configured for emitting radiation towards the pipe wall;
        a scintillation detector having an input for detecting scintillation radiation and an output for electronically transmitting a scintillation detection signal;
    an external data processing assembly adapted for placement outside of the pipe, the data processing assembly including:
        a photo-multiplier tube (PMT) having a photonic input and an electronic output;
        a gamma spectrometry multi-channel analyzer (MCA) having a display output for display of radiation peaks;
        a nuclear statistics electronics assembly having an input in operable communication with the electronic output of the photo-multiplier tube, and having an output in operable communication with the gamma spectrometry MCA, the data processing assembly being configured for measuring back-scattered gamma radiation reflected from the pipe wall; and
    at least one elongate flexible light-pipe having a first end connected to the miniaturized detection assembly and a second end connected to the photomultiplier tube, the at least one light pipe conveying the scintillation detection signal from the miniaturized detection assembly inside the pipe to the external data processing assembly outside the pipe;
    whereby the MCA display shows back-scattered gamma radiation peaks proportional to corrosion and scale inside the pipe.

2. The miniaturized pipe inspection system according to claim 1, further comprising a bias spring in mechanical contact with the miniaturized detection assembly, the bias spring being adapted for biasing the detection assembly against the wall of the pipe.

3. The miniaturized pipe inspection system according to claim 1, further comprising a gamma shield disposed between said at least one primary radiation source and said scintillation detector.

4. The miniaturized pipe inspection system according to claim 1, wherein the at least one primary radiation source has an intensity within an order of magnitude between micro-Curies and milli-Curies.

5. The miniaturized pipe inspection system according to claim 1, wherein said at least one light pipe comprises a plurality of light pipes for transmitting light signals to the PMT.

6. The miniaturized pipe inspection system according to claim 1, further comprising a gamma shield forming a collar in contact with and surrounding the scintillation detector, the at least one primary radiation source forming a second collar in contact with and surrounding the gamma shield.

7. The miniaturized pipe inspection system according to claim 1, wherein said at least one primary radiation source of gamma rays comprises a plurality of primary radiation sources of gamma rays.

8. The miniaturized pipe inspection system according to claim 1, wherein said at least one primary radiation source of gamma rays is in direct contact with the scintillation detector.

9. The miniaturized pipe inspection system according to claim 8, wherein said at least one primary radiation source of gamma rays comprises a coating on the scintillation detector.

10. The miniaturized pipe inspection system according to claim 1, further comprising means for converting signals of translational and rotational movement of the miniaturized detection assembly into an image showing corrosion and scale inside the pipe following scanning of the pipe.

11. The miniaturized pipe inspection system according to claim 1, wherein the pipe is a twisted pipe.

12. The miniaturized pipe inspection system according to claim 1, wherein the pipe is a bent pipe.

13. The miniaturized pipe inspection system according to claim 1, wherein the pipe is a pipe of non-circular cross section.

14. The miniaturized pipe inspection system according to claim 1, wherein the pipe is a prepared pipe surface.

15. The miniaturized pipe inspection system according to claim 1, wherein the pipe is an unprepared pipe surface.

* * * * *